United States Patent [19]

Cotey

[11] 4,225,423
[45] Sep. 30, 1980

[54] OVA DETECTOR ASSEMBLY

[76] Inventor: John Cotey, 27 W. End Ave., Haddonfield, N.J. 08033

[21] Appl. No.: 37,361

[22] Filed: May 9, 1979

[51] Int. Cl.³ .............................................. B03B 7/00
[52] U.S. Cl. ........................................ 209/3; 209/17; 73/425.2
[58] Field of Search ................. 209/17, 173, 250, 268, 209/273, 3; 422/101, 102; 23/230 B; 73/425, 425.2

[56] References Cited

U.S. PATENT DOCUMENTS

| | | | |
|---|---|---|---|
| 2,835,246 | 5/1958 | Boettger | 73/425.2 X |
| 3,819,045 | 6/1974 | Greenwald | 209/17 |
| 3,905,895 | 9/1975 | Addis | 209/17 |
| 3,936,373 | 2/1976 | Studer | 209/17 |
| 3,963,119 | 6/1976 | Lukacs et al. | 210/516 X |
| 4,081,356 | 3/1978 | Zierdt | 209/17 X |

*Primary Examiner*—Ralph J. Hill
*Attorney, Agent, or Firm*—Eugene E. Renz, Jr.

[57] ABSTRACT

A device for use in examing fecal matter for presence of ova. The device essentially comprises a cup shaped vial open at one end and an elongated strainer adapted to nest and seat in the vial and a closure cap which may be pivotally connected to the vial. The vial has a mixing blade in its vase and the strainer has a sampler cavity at one axial end with inwardly directed fins which engage over the blade in the fully assembled position so that when a solution is added and a specimen has been accumulated in the sampler cavity of the strainer it may be oscillated relative to the container to effect good mixing and release of ova from the feces. The vial and strainer have interengaging lug and rib means to limit rotation of the strainer in the vial. The vial also is formed with a configuration of openings in a radial wall which have faces which converge downwardly to a sharp edge to ensure smooth and unobstructed flow of ova to the head section of the strainer. The strainer nests loosely in the vial initially for ease of removal of the strainer to accumulate a specimen and thereafter can be seated firmly in place to provide a liquid seal.

7 Claims, 25 Drawing Figures

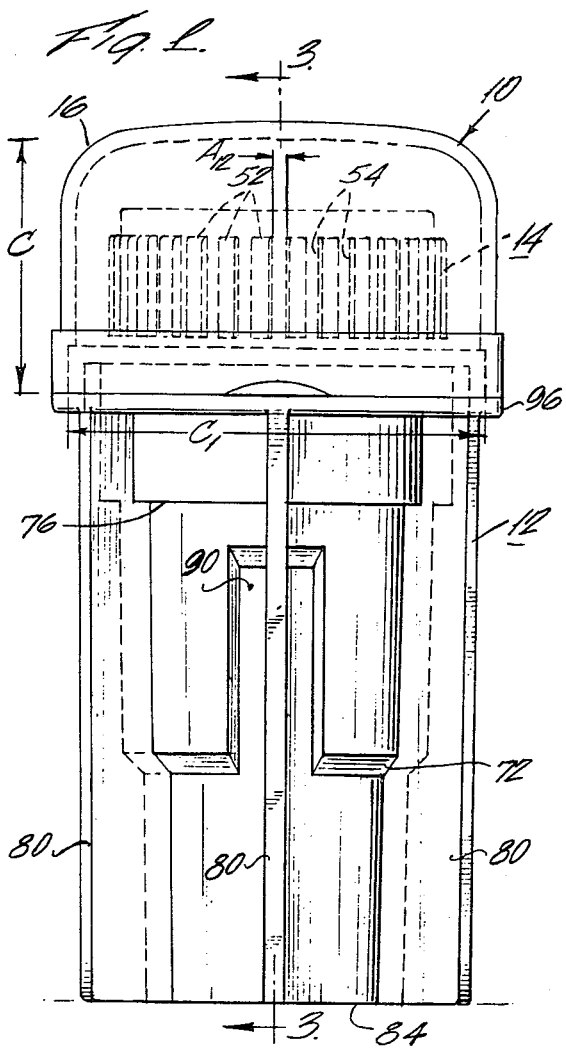
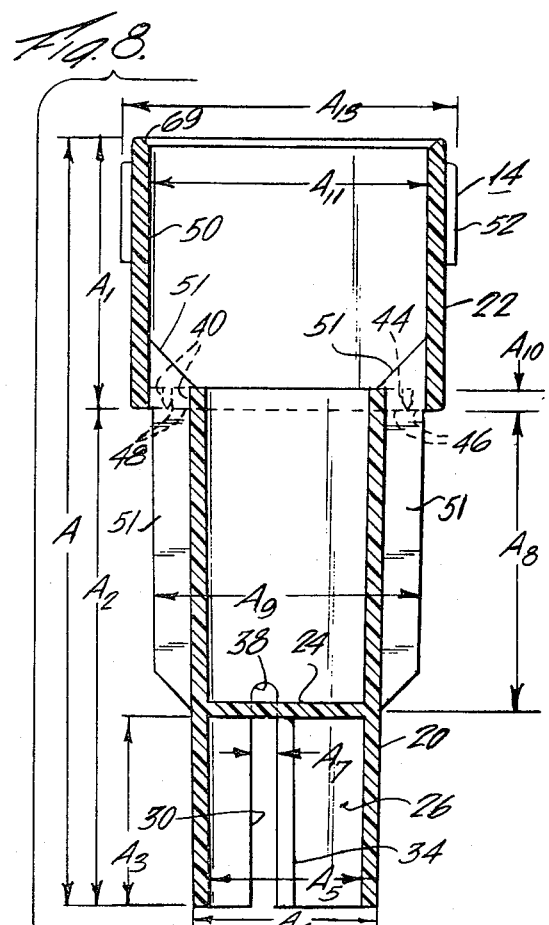
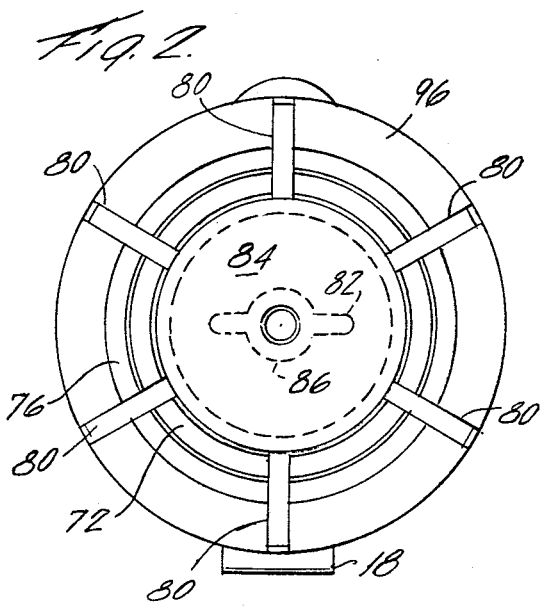
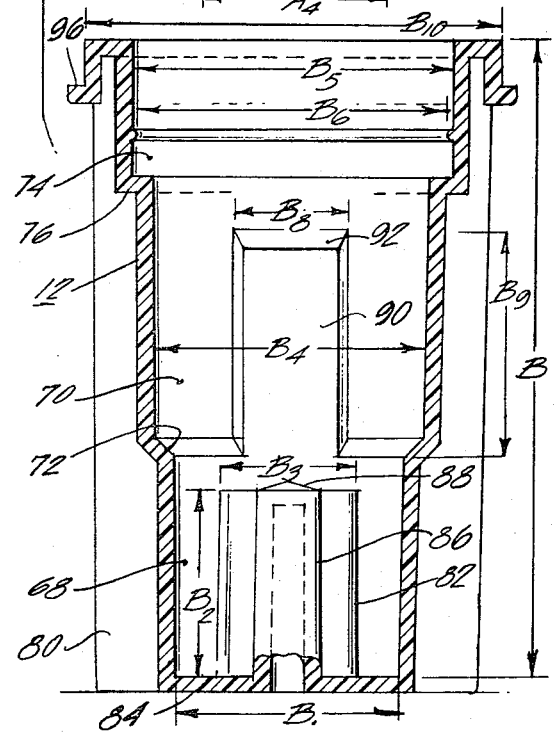

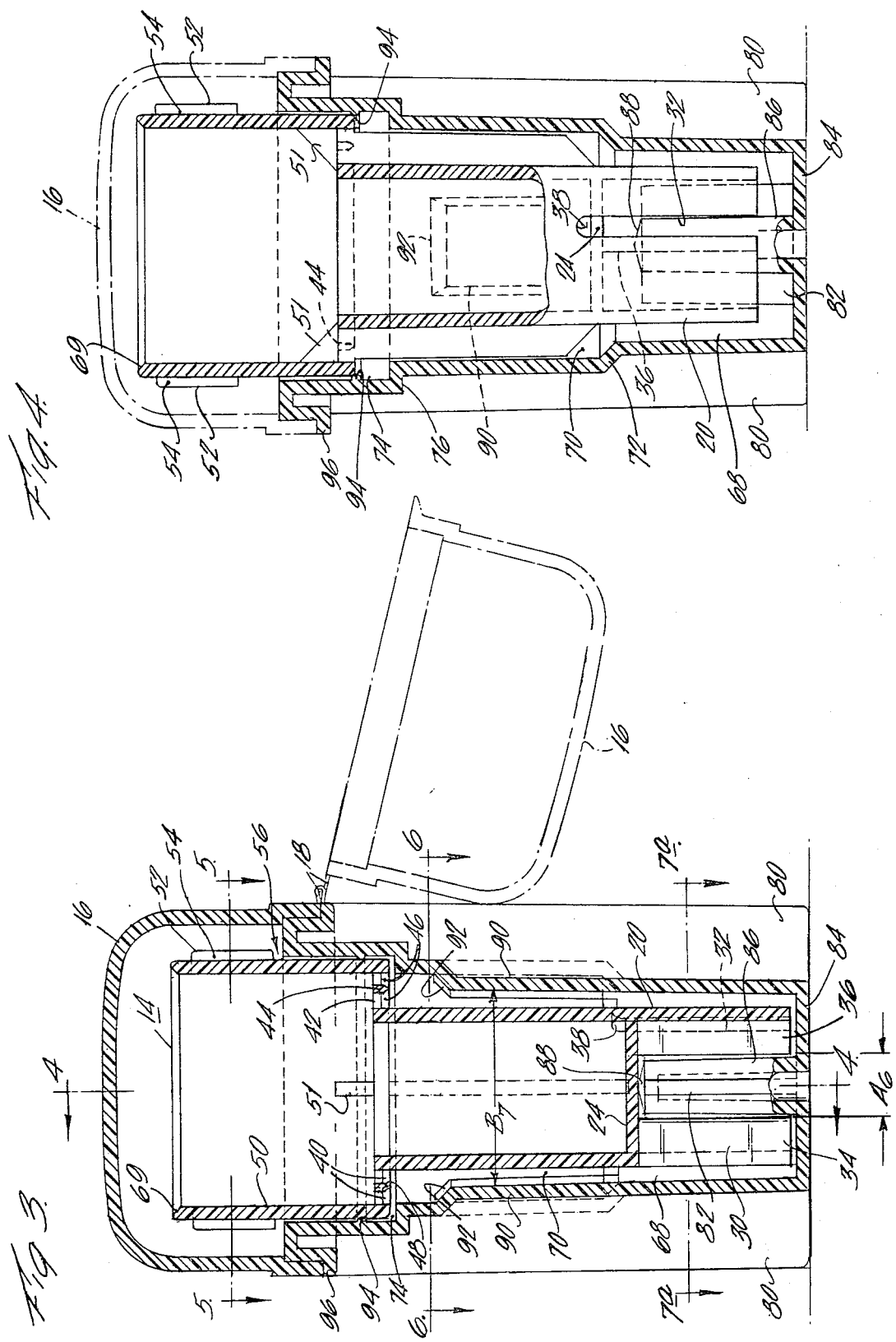

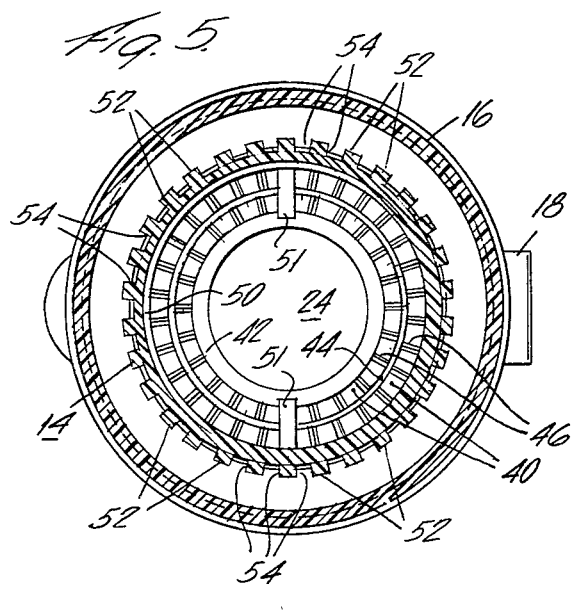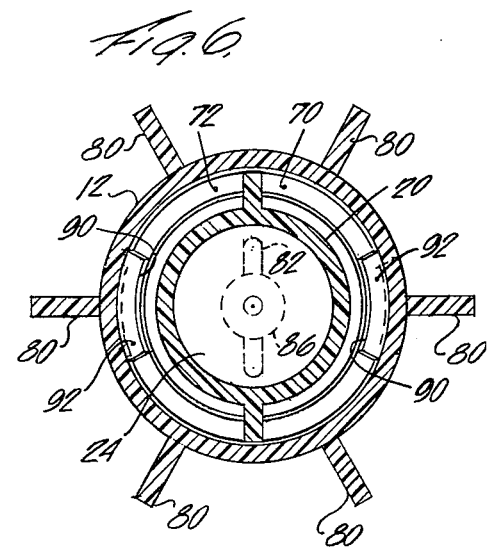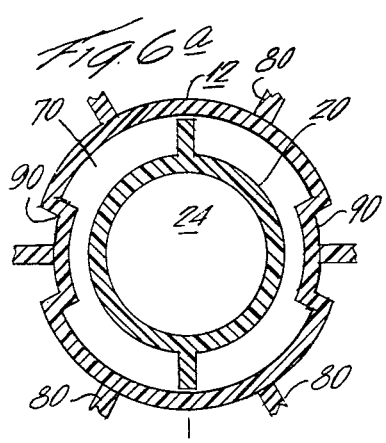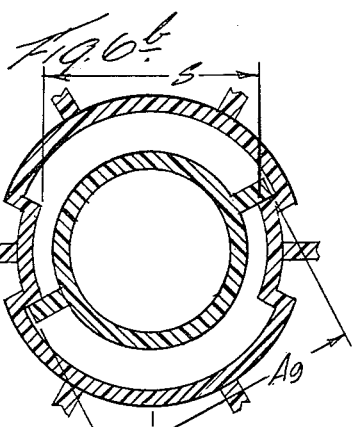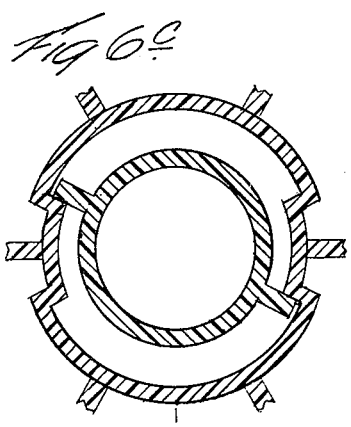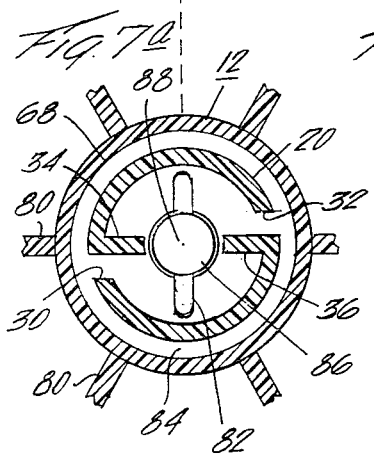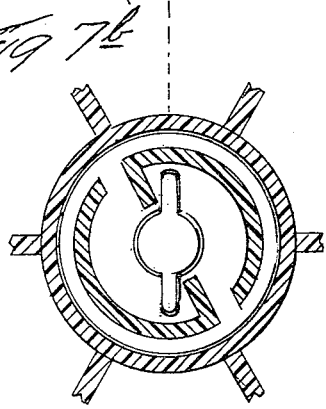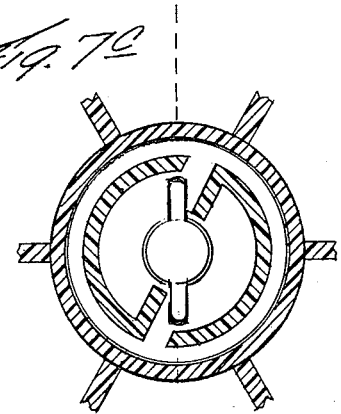

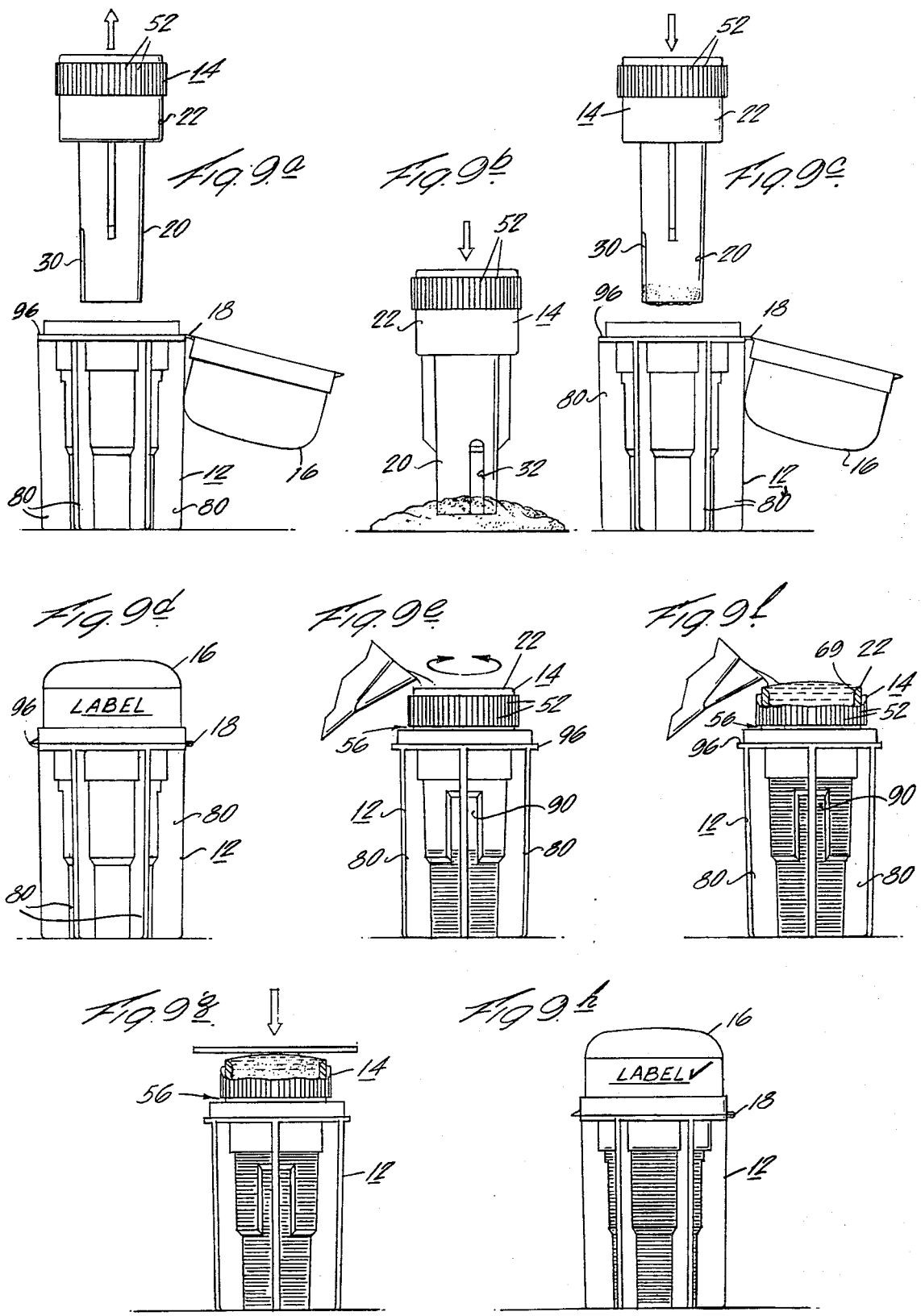

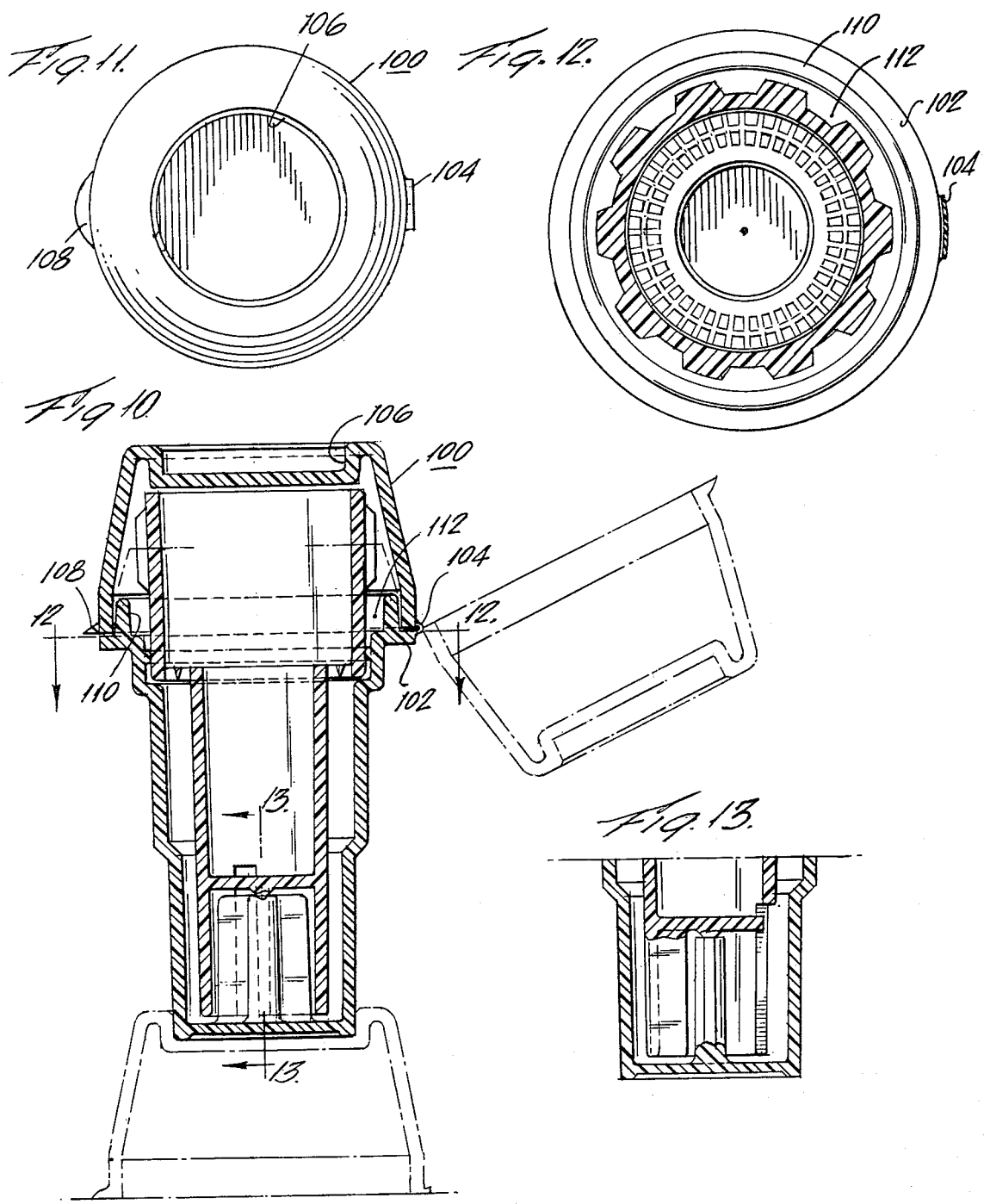

OVA DETECTOR ASSEMBLY

BACKGROUND OF THE INVENTION

The present invention relates to an assembly for use in examining fecal matter to determine the presence of ova or eggs of parasites which may be present therein. More specifically, the present invention is characterized by novel features of construction and arrangement providing a unit facilitating easier and more sanitary handling of the fecal matter and including a novel mixing or separating means to ensure good sampling of the ova present in the specimen examined.

Apparatus and method for examining fecal matter for the presence of ova are not new per se. For example, the Studer U.S. Pat. No. 3,936,373 shows a device for this purpose. The unit shown is an elongated thimble of generally cylindrical shape peculiarly adapted to be inserted into a standard container, the thimble having the plurality of small openings or perforations in its cylindrical sidewall. The openended top of the thimble is provided with a circumferentially extending outwardly projecting flange configuration for securing the thimble in place in a container. In using the Studer unit and as set forth in Column 5, the user fills the container to approximately one-tenth of its depth with the fecal matter. Then in the laboratory any excess is removed and discarded using a disposable wooden or plastic spatula. An amount of flotation liquid is then added to the receptacle. The receptacle or container is then capped and thoroughly shaken to mix the liquid with the sample feces. The cap is then removed and the thimble is inserted into the top of the transport receptacle. As the thimble gravitationally settles in place under its own weight, the mixture rises in the annular space between the inside of the receptacle and outside of the thimble. When the thimble reaches the bottom of its free fall, the operator presses the thimble to engage the locking flange to the operator. Additional quantities of solution are added to form a slight meniscus. The technician then places a microscope cover glass on the meniscus surface to pick up the surface liquid and the entrained ova. When the test is completed the cap is applied and the container and thimble are discarded.

The Greenwald U.S. Pat. No. 3,819,045 shows a unit for a similar purpose. The device comprises a base having a central shallow well providing a receptacle area for fecal matter, a cylindrical double open ended tube which fits over this base to form a container and a separate perforated piston. A disposable spatula or spoon is used to deposit a quantity of fecal matter in the small well of the base. The cylinder is then assembled to the base around the well and partially filled with a flotation liquid. The mixture is then stirred with a disposable dowel. The piston-like strainer is then manually pressed into the cylinder to force the suspended fecal matter toward the base to a point where the outer end of the piston rod is located below the top edge of the cylinder so that it does not interfere with the meniscus or slide placed over the open top end of the cylinder. A second filling operation then takes place to raise the level of the flotation liquid to the top edge of the cylinder.

The above devices while appearing to be of simplified construction, nevertheless have several obvious disadvantages and drawbacks which the present invention is designed to overcome. For example, in each case, a spatula or spoon is needed to accumulate the fecal matter specimen. This procedure is both time consuming and messy. Furthermore, the spatula is a separate contaminated element which must be discarded before the operator can proceed with the rest of the procedure.

Additionally, in these units, either the thimble or piston have to be further manipulated by the user after flotation liquid has been added. Oftentimes this results in spillage or contact of the operator's hand with the solution. It has also been observed that since neither unit has direct contact agitation or stirring means, maximum separation of ova is not realized, thus contributing to the already unpleasantness of the procedure and increases the possibility of contaminating the operator and laboratory.

SUMMARY OF THE INVENTION

The present invention provides a fecal analyzer of relatively simplified construction which can be manufactured easily and economically and is, therefore, disposable. The unit is characterized by novel features of construction and arrangement which minimize the risk of contamination to operator and laboratory and, therefore, is esthetically more desirable. The unique agitation and mixing arrangement produces more reliable and more accurate test results. Thus the assembly of the present invention comprises an elongated strainer element, the outer tip end of which is shaped to form a scoop for a desired quantity of fecal matter and which nests in a vial having a mixing element in its base. The tip of the strainer and mixing element interengage to achieve good mixing and separation of the ova in a closed environment. By reason of the fact that a precise premeasured quantity of the fecal matter may be easily accumulated in the unit outside the laboratory, the result is that the laboratory personnel do not have close contact with the fecal matter and therefore, the procedure diminishes the possibility of contaminating the operator and the laboratory.

Another feature of the present invention is the particular configuration and arrangement of the strainer and vial whereby they nest initially with a loose fit and allow for an outer closure cap to be assembled in place. This has the advantage that the user simply removes the cap and now can withdraw the strainer readily to accumulate the precise amount of specimen in the sample cavity and then insert the strainer back in the vial. When the strainer is finally seated by simply pressing it axially in place, the desired liquid seal is created prior to filling the assembly with the flotation liquid thereby eliminating the problem of spillage.

Another feature is the two-point pivot bearing which facilitates easy rotation of the strainer to thoroughly mix the fecal matter and release the ova. The strainer and vial are provided with internal stops to limit relative rotation to oscillating movement of the strainer, the stops also ensuring assembly of the strainer in the vial without damaging the interengaging mixing elements.

The strainer is also provided with a series of axially directed, circumferentially spaced ribs adjacent the open end thereof which in the seated relation terminate just short of the top end of the container wall which they confront to provide an annular capillary channel for overflow.

Still another feature is the provision of a series of openings in a radial wall of the strainer which have downwardly bevelled edges defining the openings whereby the eggs floating to the meniscus are diverted to flow through the openings and do not accumulate on the intermediate strainer wall.

BRIEF DESCRIPTION OF THE DRAWINGS

These and other objects of the present invention and the various features and details of the operation and construction thereof are hereinafter more fully set forth with reference to the accompanying drawings wherein:

FIG. 1 is a side elevational view of a fecal analyzer assembly in accordance with the present invention;

FIG. 2 is a bottom plan view thereof;

FIG. 3 is a transverse sectional view taken on lines 3—3 of FIG. 1, the closure cap being shown in broken lines in an open position;

FIG. 4 is a transverse sectional view taken on lines 4—4 with the strainer in a loosely held position in the vial, this being the position of the unit prior to use in accumulating a specimen;

FIGS. 5 and 6 are sectional views taken on lines 5—5 and 6—6 respectively of FIG. 3;

FIGS. 6a, 6b and 6c are sectional views similar to FIG. 6 showing the strainer in different angular positions in the vial and illustrating the interengaging stop means for limiting rotation of the strainer;

FIG. 7a is a sectional view taken on lines 7a—7a of FIG. 3;

FIGS. 7b and 7c are sectional views similar to FIG. 7a showing the strainer rotated between opposite limit positions;

FIG. 8 is an exploded transverse sectional view of the strainer and vial;

FIGS. 9a-9h inclusive are views showing the analyzing procedure employing a fecal analyzer in accordance with the present invention;

FIG. 10 is a transverse sectional view of still another embodiment of fecal analyzer in accordance with the present invention;

FIG. 11 is a top plan view thereof; and

FIG. 12 is an enlarged sectional view taken on lines 12—12 of FIG. 10; and

FIG. 13 is a fragmentary sectional view taken on lines 13—13 of FIG. 10.

DESCRIPTION OF THE PREFERRED EMBODIMENTS

Referring now to the drawings and particularly to FIGS. 1 and 8 thereof, there is illustrated a fecal analyzer assembly constructed in accordance with the present invention generally designated by the numeral 10. The assembly consists essentially of three basic elements, a vial or open-ended container 12, a strainer unit 14 which nests in the vial and closure or dome-shaped cap 16 which may be connected to the container by a flexible hinge 18. Considering the broad structural details and arrangement of the assembly in terms of function, the strainer unit has an elongated generally cylindrical tip portion which has a cavity formed in its lower terminal end defining a scoop for a predetermined quantity of fecal specimen, an enlarged head portion and an annular array of openings of a prescribed dimension and configuration in the radial wall at the juncture of the tip and head portion providing a strainer through which the ova to be examined passes. The vial has an upwardly projecting blade in its base which cooperates with the tip portion of the strainer to serve as a means for mixing the fecal specimen in the solution to release the ova from the fecal matter. The head portion of the vial and the strainer are of a given complementary configuration and size explained in more detail below whereby the strainer seats loosely in the vial to permit easy removal by the user for gathering a specimen and then can be inserted in place to provide an effective seal during the mixing phase of the processing or examination cycle.

Referring now to FIGS. 9a-9h which illustrate stepwise the fecal examing procedure utilizing the assembly of the present invention. An operator desiring to gather a specimen, simply flips the cap to the position shown in FIG. 3 and grips the head portion of the strainer to withdraw it from the vial. (FIG. 9a) A predetermined quantity of the fecal matter for use as a specimen is then gathered in the tip or sample cavity of the strainer by manipulation of the strainer in much the same manner as a cookie cutter. (see FIGS. 9b and 9c) This permits gathering in a very sanitary manner of the desired quantity of the fecal matter specimen. The strainer is then placed back into the vial seating it in a sealed position. (FIG. 9d) The vial is then filled approximately half way with a flotation solution to float or levitate the parasite ova or eggs in the fecal matter. (FIG. 9e) Typical solutions for this purpose are sodium nitrate, sucrose, magnesium sulfate, zinc sulfate or sodium chloride. The purpose of the solution is to raise the specific gravity so that the ova will float, the ova in such mixture having a specific gravity less than that of the solution. The head portion of the strainer which projects beyond the vial is gripped by the user and oscillated to effect mixing of the specimen in the solution and release of the ova. After thorough mixing in this fashion, an additional quantity of solution is added in the manner shown in FIG. 9f to raise the level to a meniscus beyond the top edge of the strainer. A slide is then placed on the meniscus formed and after a predetermined time removed. A cover slip is then placed on the slide and the slide is ready for examination under a microscope. (FIG. 9g) After removal, the cap can be flipped in place to seal the unit and the entire assembly can be discarded in a sanitary fashion. (FIG. 9h)

Considering now more specifically the structural details and arrangement of the assembly the strainer unit 14 comprises a generally elongated hollow cylindrical tip section 20 and an enlarged head portion 22. The tip section 20 has an intermediate base or wall 24 spaced from the terminal end defining a pocket or scoop 26 of a given size for the fecal specimen. The tip portion below the base 24 is slotted axially at diametrically opposed locations 30, 32 and includes radially inwardly directed short fin sections 34, 36 which cooperates with the blade to mix the fecal matter and and effect release of the ova. Note that the axial slots 30, 32 extend slightly beyond the base to provide sidewall openings 38 permitting flow of solution therethrough.

The strainer includes means for separating the ova from the fecal matter to permit flow of ova upwardly in the vial to the meniscus and retain the fecal matter in the lower part. The strainer or separating means, in this instance, is formed by a series of openings 40 of a predetermined size and configuration in the radial wall 42 at the juncture of the intermediate section and head section of the strainer. (see FIGS. 3 and 8) These openings are defined by a network of dividers including a circumferentially extending intermediate wall 44 and a series of radial connecting bridges 46 between the intermediate section and the head section. The wall 44 and bridges 46 have sharply angled faces 48 to divert ova so that they flow upwardly through the openings 40 into the head section and are not blocked as would be the case if the wall sections were simply flat. (see FIGS. 3 and 8) Another factor contributing to good flow of the ova is the alignment of the inner peripheral wall 50 of the head section 22 with the intermediate wall section of the vial as best illustrated in FIG. 3. Triangular gussets 51 for strength and rigidity span the head section and the strainer openings.

In the fully seated position of the strainer in the vial, the strainer may be oscillated through a limited range as illustrated in FIGS. 7a–7c. These elements are, however, somewhat fragile and, therefore, to prevent breakage by reason of the user attempting to rotate the strainer continuously rather than oscillate it, the assembly is provided with limit stop means. This means includes, in part, a pair of lugs 51, 51 projecting from the intermediate section of the strainer at diametrically opposed locations which are offset angularly, in the present instance, 90° relative to the fin sections 34, 36. (see FIG. 8) The lugs extend from the head section to a point adjacent the base 24 and as illustrated have upwardly divergent bevelled lower edges. These lugs cooperate and engage with internal stops in the vial slightly before the strainer is rotated to the opposite limit positions shown in FIGS. 7a–7c.

The head section of the strainer has a series of ribs 52 on its outer periphery which are of a predetermined size and spacing to define capillary grooves 54 therebetween. The ribs extend down the sidewall of the head section to a predetermined depth to form with the upper axial end face of the vial an annular capillary groove 56 to entrap any slight spillage which may occur when filling the vial with solution to form the meniscus. The upper axial end face of the strainer is bevelled inwardly as at 69 to provide a relatively sharp edge seat for the slide for ease of removal.

Considering now the structural details of the vial 12 and specifically with reference to FIG. 8, the vial 12 is an elongated hollow container open at its upper end and, in the present instance, is of tiered construction defining a lower mixing chamber 68, an intermediate section 70 of the larger cross section merging with the mixing chamber 68 in a tapered wall portion 72 and an upper pilot section 74 of larger cross section than the intermediate section and connected thereto by a radial wall 76. In the present instance there are a series of axially extending circumferentially spaced ribs 80 which project radially from the outer sidewall of the container and run the full length thereof to provide a larger base area to stabilze the unit when it is placed on a table top or the like during the mixing and filling phase.

A mixing blade 82 projects upwardly from the base 84 of the vial which as illustrated has a central post 86 with a conical pivot 88 in its upper face on which the base 24 seats for ease of rotation of the strainer relative to the blade. The blade 82 is of a width $B_3$ slightly less than the diameter $A_5$ of the strainer pocket or scoop to allow for free rotational movement of the strainer relative to the blade. It is also of a predetermined axial height $B_2$ relative to the axial depth $A_3$ of the pocket so that the pivot points engage allowing for a clearance at the base of the vial also to allow for unobstructed limited rotational movement of the strainer.

Another feature of the assembly is the provision of means for limiting rotational movement of the strainer relative to the blade to prevent breakage of the blade and tip portion of the strainer, this means also serving to properly index the strainer relative to the container when it is fully seated therein. To this end, the inner sidewall of the vial is provided with a pair of diametrically opposed radially inwardly projecting ribs 90 which as illustrated have a bevelled upper face 92. The ribs 90 project inwardly and have their inner walls shaped so that they are projections of the inner surface of the mixing chamber. The ribs 90 are offset 90° to the blade. The spacing S between the confronting faces of the ribs 90 is less than the spacing $A_9$ between the outer edges of the strainer lugs 51 so that the lugs engage the ribs upon rotation of the strainer approximately 180°. The ribs, however, are of an arcuate dimension to ensure contact of the lugs with the sidewalls of the ribs before the strainer fins engage the mixing blade at opposite limit positions (see FIGS. 6a–6c and FIGS. 7a–7c). The dimensional relationship between the lugs and ribs also prevents full seating of the strainer in the vial except when the fins 34 and 36 are offset relative to the mixing blade and pass freely thereover. For example, if a user inserts the vial with the lugs aligned with the ribs 90, the bevelled edges of the lugs will engage the bevelled ribs of the vial and the user will have to rotate the strainer slightly to an offset position to achieve complete assembly.

The upper or seal section of the vial is formed with a circumferentially extending bead 94 spaced upwardly a predetermined distance from the juncture from the seal and intermediate sections. The bead forms a tight fit with the head portion of the strainer in the partially and fully seated position to establish a liquid seal at that juncture. The configuration of the head portion of the strainer and the seal section of the vial is such that the inner peripheral wall of the strainer head section forms a continuation of the inner sidewall of the intermediate section of the vial to ensure good flow of ova to the strainer section thereby ensuring optimum flotation of ova to the meniscus. The seal section of the container has an outwardly directed flange 96 below its upper edge forming a seat for the cap or closure lid.

As described above, there are certain dimensional relationships between the various elements of the strainer, vial and cap which provide certain functional objectives and advantages. For example, the axial depth of the strainer specimen pocket and height of the mixing blade and width or diametral relationships are such to space the elements so that the only bearing point is at the pivot location thereby facilitating free, unobstructed limited rotation of the parts relative to one another. Additionally the interior rib in the vial and the outward lugs on the strainer are of a predetermined dimensional relation to ensure against improper assembly of the strainer into the vial. Also the various diametral relationships between the head section of the strainer and the seal section of the vial are such to provide a loose fit of the strainer for initial assembly of the parts and to provide a tight liquid seal when the strainer is pressed home to an operative position for mixing and stirring the fecal matter. Even though various dimensional relationships may be utilized to produce an assembly achieving the above described objectives, the following is an example of an assembly made in accordance with the present invention setting forth specific dimensions which have been found to be operative to produce the desired results.

"A" CHART

Strainer Dimensions

A—Overall length—2.118"
$A_1$—Enlarged head portion length—0.743"
$A_2$—Elongated hollow cylindrical tip section, length—1.375"
$A_3$—Distance of intermediate base or wall from bottom edge of cylindrical tip section—0.520"
$A_4$—Outside diameter of bottom of cylindrical tip section—0.509" diameter
$A_5$—Inside diameter of bottom of cylindrical tip section—0.438" diameter
$A_6$—Distance between radially inwardly directed short fin sections—0.190"
$A_7$—Width of elongated slots—0.060"
$A_8$—Length of lugs mounted to outer wall of cylindrical tip section from bottom of enlarged head section—0.800"
$A_9$—Distance between outer edges of lugs on cylindrical tip section—0.750"
$A_{10}$—Thickness of strainer section—0.060"
$A_{11}$—Inner diameter of head section—0.774"
$A_{12}$—Distance between knurling lands on enlarged head—0.050"
$A_{13}$—Outer diameter of knurling lands on enlarged head—0.935"

"B" CHART

Vial Dimensions

B—Overall length "inside"—1.750"
$B_1$—Inner diameter at base of vial (lower mixing chamber)—0.635"
$B_2$—Height of center post from inner bottom of vial—0.520"
$B_3$—Distance between outer edges of mixing blade—0.398"
$B_4$—Inner diameter of intermediate section—0.774"
$B_5$—Inner diameter of pilot section—0.885" diameter
$B_6$—Inner diamter of bead—8.64" diameter
$B_7$—Inner diameter of projecting ribs—0.635" diameter
$B_8$—Width of projecting ribs (inner)—0.240"
$B_9$—Length of inwardly projecting ribs from tapered wall portion—0.593"
$B_{10}$—Outer diameter of pilot section—1.155" diameter

"C" CHART

Cap Dimensions

C—Inner height of cap—0.537"
$C_1$—Inside dimension of cap open end—1.155 diameter There is illustrated in FIGS. 10-13, another embodiment of fecal analyzer assembly in accordance with the present invention. This embodiment of the invention is similar to that described previously in many respects and accordingly, reference numeral for those parts which are identical have been assigned the same reference numeral and new structure has been assigned new identification numerals.

In accordance with this embodiment, the closure cap 100 which may be connected to an annular flange 102 projecting radially from the upper end of the vial by a flexible hinge 104 and has an indentation 106 formed in its top. This indentation is preferably of a diameter slightly greater than the diameter of the base of the vial so that it may be removed at the hinge and used as a base for supporting the vial and strainer during the examination procedure. As noted, the cap 100 has a thumb tab 108 at a point located diametrically opposite the hinge engageable by the finger of the operator to actuate it when it is desired to pivot the cap to an open position. The radial flange at the upper end of the vial has an axially upwardly projecting lip 110 spaced from the inner wall and extending outwardly beyond the outer periphery of the strainer to define an annular overflow basin 112 in the event that the operator fills the strainer slightly beyond its capacity.

While particular embodiments of the invention have been illustrated and described herein, it is not intended to limit the invention and changes and modifications may be made therein within the following claims.

What is claimed is:

1. A device for use in examining fecal matter for presence of ova comprising a vial open at one end, mixing means in the base of said vial remote from said open end, an elongated hollow strainer including a cup-like compartment at one terminal end adapted to contain a predetermined quantity of feces, the cup-like compartment engaging over said mixing means when the strainer is fully seated in the vial and adapted for limited oscillating movement relative to the vial to mix the feces and ensure good release of ova when a solution is added to the device.

2. A device as claimed in claim 1 wherein said mixing means comprises a blade projecting upwardly from the base of the vial of a maximum cross sectional dimension smaller than the diameter of the cup-like compartment at said one terminal end of the vial, and wherein said compartment is formed with at least one fin section, cooperatively associated with said blade to produce good mixing of a fecal specimen.

3. A device as claimed in claim 2 including a pair of ribs on the interior wall of the vial and wherein said strainer includes a pair of lugs, the lugs and ribs being selectively oriented relative to the mixing blade so that upon rotation of the vial the strainer lugs engage the ribs to limit rotation of the strainer and prevent engagement of the fin section and mixing blade.

4. A device as claimed in claim 2 wherein said mixing blade includes a post section with a tip projecting beyond the upper edge of the blade engageable with a wall spaced from the lower terminal edge of the strainer defining the base of the cup-like compartment providing a two point pivot facilitating easy rotation of the strainer relative to the vial.

5. A device as claimed in claim 1 wherein said strainer comprises enlarged head section connected to the tip of the vial by a radial wall and including means defining a plurality of openings in the radial wall.

6. A device as claimed in claim 5 wherein said openings are defined by a gridwork whose edges are sharply angled faces which converge to a sharp edge thereby to provide for more fluid flow of ova without obstruction to the head section of the strainer.

7. A device as claimed in claim 5 wherein the vial has an enlarged pilot section and includes a circumferentially extending radially inwardly directed rib, said head section of the strainer engaging said rib to provide a seal and the interior wall of the vial aligning with the interior wall of the head section of strainer when the strainer is fully seated in the vial.

* * * * *